United States Patent [19]

Gates et al.

[11] Patent Number: 4,639,431

[45] Date of Patent: Jan. 27, 1987

[54] CATALYSTS IN FISCHER-TROPSCH PROCESS FOR PRODUCING OLEFINS

[75] Inventors: William E. Gates, Somerset; Rocco A. Fiato, Scotch Plains, both of N.J.

[73] Assignee: Exxon Research and Engineering Company, Florham Park, N.J.

[21] Appl. No.: 754,003

[22] Filed: Jul. 11, 1985

[51] Int. Cl.$^4$ .................. B01J 23/10; B01J 23/78; B01J 23/80

[52] U.S. Cl. ..................... 502/304; 502/302; 502/303; 502/524

[58] Field of Search ............ 502/304, 524, 302, 303

[56] References Cited

U.S. PATENT DOCUMENTS

| | | | |
|---|---|---|---|
| 3,615,807 | 10/1971 | Yates | 106/288 |
| 3,932,551 | 1/1976 | Grasselli et al. | 260/680 |
| 3,992,328 | 11/1976 | Sze et al. | 252/459 |
| 4,001,317 | 1/1977 | Grasselli et al. | 260/533 |
| 4,162,234 | 7/1979 | Grasselli et al. | 252/432 |
| 4,186,112 | 1/1980 | Vogt et al. | 252/471 |
| 4,199,523 | 4/1980 | Rottig | 260/449.6 R |
| 4,211,673 | 7/1980 | Lewellen et al. | 252/462 |
| 4,291,126 | 9/1981 | Sugier et al. | 518/713 |
| 4,537,867 | 8/1985 | Fiato et al. | 502/74 |

FOREIGN PATENT DOCUMENTS

| | | |
|---|---|---|
| 0506064 | 5/1939 | United Kingdom . |
| 833976 | 5/1960 | United Kingdom . |
| 1512743 | 6/1978 | United Kingdom . |
| 1553361 | 9/1979 | United Kingdom . |
| 1553362 | 9/1979 | United Kingdom . |
| 1553363 | 9/1979 | United Kingdom . |

*Primary Examiner*—W. J. Shine
*Attorney, Agent, or Firm*—Edward H. Mazer; E. Thomas Wheelock

[57] ABSTRACT

New catalysts containing a Group VIII metal such as iron, a Group IIB metal, such as zinc, a Group IA alkali metal such as potassium, rubidium and/or cesium, and a lanthanide metal, such as cerium, exhibit improved productivity in synthesis of alpha-olefins from hydrogen rich synthesis gas.

12 Claims, No Drawings

CATALYSTS IN FISCHER-TROPSCH PROCESS FOR PRODUCING OLEFINS

BACKGROUND OF THE INVENTION

1. Field of the Invention

This invention relates to cerium-containing, iron-based catalysts, not containing a Group IVB or Group VIIB metal, and their use in Fischer-Tropsch processes for producing alpha olefins.

2. Brief Description of the Prior Art

The search for processes to provide alternate feedstocks for chemicals, and particularly low molecular weight olefins, has been prompted by the growing shortage of traditional petroleum reserves, as well as the increasing instability of international hydrocarbon sources.

One approach to the problem has been the utilization of the Fischer-Tropsch synthesis in producing a selective product distribution of olefinic hydrocarbons also containing paraffins, in varying olefin/paraffin ratios, depending on the catalyst composition and reaction conditions. Various catalyst combinations of elements have been tested in the past, of which the chief constituent element has been nickel, cobalt, iron or ruthenium. Secondary products in the processes included branched chain hydrocarbons, aliphatic alcohols, aldehydes and acids.

Ruhrchemie Aktiengesellschaft has disclosed in GB No. 1,512,743, GB No. 1,553,361, GB No. 1,553,362 and GB No. 1,553,363 catalysts pertaining to the selective production of $C_2$–$C_6$ olefins from synthesis gas (preferably carbon monoxide and hydrogen). The inventions embody a process for the production of one or more unsaturated hydrocarbons comprising catalytic hydrogenation of a carbon oxide with hydrogen at 250° C. to below 350° C. and a total pressure of 10 to 30 bars in the presence of a catalyst which contains (a) one or more oxides selected from difficult-to-reduce oxides of metals from Group IVB of the Periodic Table or a lower oxide of Group V and/or Group VII; and (b) one or more metals selected from the Group VIII of the Periodic Table, the ratio by weight of the metal or metals of the one or more oxides (a) to the one or more metals (b) being in the range 1:2 to 1:10. Additionally, the catalysts can contain Group 1A alkali metal, MgO and ZnO promoter agents. In the process good yields of unsaturated hydrocarbons, especially gaseous olefins, are reported.

U. K. Pat. No. 833,976 discloses a catalyst for the production of ethylene from CO and hydrogen consisting of four components: the first a group including zinc oxides; the second group preferably being cobalt, although iron also could be used with the claimed proviso that the Group VIII metal component constitute not more than 10% of the total weight of the catalyst, and being activated by compounds which may include manganese oxide; the third group including an oxide of titanium and/or the rare earth elements; and the fourth group being a carbonate, oxide or hydroxide of an alkali metal. The reaction preferably is conducted at a temperature of from 350° C. to 520° C., preferably from 350° C. to 450° C.

U. K. Pat. No. 506,064 discloses the preparation of an iron-containing Fischer-Tropsch catalyst. The catalyst also may contain amounts of alkali compounds which are practically decomposed up to 1,000° C. This patent also discloses a lengthy list of other compounds that may be added, including titanium, manganese and cerium oxides or hydroxides.

U.S. Pat. No. 4,199,523 discloses a Fischer-Tropsch catalyst containing at least 60% iron. In addition, promoters, such as copper and/or silver and alkali, are desirable. Other additives, such as alkaline earth metal compounds, zinc oxide, manganese oxide, cerium oxide, vanadium oxide, chromium oxide, and the like may also be used.

U.S. Pat. No. 4,291,126 discloses a catalytic process for the manufacture of linear saturated alcohols from CO and $H_2$. The catalyst comprises copper, cobalt, a third metal selected from chromium, vanadium and manganese.

U.S. Pat. No. 4,211,673 discloses a catalyst composed of a rare earth metal, such as cerium, and a transition metal, such as iron, for the reduction of CO to produce oxygenated hydrocarbons.

U.S. Pat. No. 4,186,112 also discloses a Fischer-Tropsch catalyst which may include cerium.

Other patents which disclose the use of cerium include U.S. Pat. Nos. 4,162,234; 4,001,317; 3,992,238; 3,932,551; and 3,615,807.

However, what is desired in the art and which none of the above-identified art disclosures teach is the process combination technique of significantly increasing the activity of a low molecular weight olefin producing catalyst while concurrently maintaining a high olefins product slate under standard olefin producing conditions.

SUMMARY OF THE INVENTION

It has been discovered that a sintered, iron-containing spinel combination metal oxide catalyst containing an element or elements from the lanthanide series (90-103), such as cerium, enhances the catalyst activity and maintains a high olefins/paraffins product distribution during a Fischer-Tropsch α-olefin synthesis.

It has also been discovered that, under selected conditions of temperature and pressure in conjunction with the catalyst described above, one can also obtain unsaturated hydrocarbons of low molecular weight in good yield. Alternatively, higher molecular weight species may be obtained under suitable conditions.

The catalyst may be prepared by contacting a composition comprising an element or elements from Group VIII, IIB, IA and an element or elements from the lanthanide series. The preparation of the catalyst employed in the process of the invention may be initiated from a variety of precursors. The manner and means of integrating these precursors to a final state of the catalyst may be accomplished utilizing standard practice techniques, such as blending, co-precipitating, impregnation, fusion and the like. The following disclosure will illustrate to one skilled in the art several preferred examples of catalyst composition preparation, reactivity, selectivity and activity.

The catalyst comprises about 65 to 95 weight percent of Group VIII metal oxides, such as the oxides of Fe, a Group IIB metal oxide, such as ZnO, ranging from 5 to 20 weight percent, a Group IA metal oxide, such as $Cs_2O$, ranging from 1 to 10 weight percent; and a Lanthanum group metal oxide, such as $CeO_2$, ranging from about 1 to 10 weight percent.

By this invention there is provided a hydrocarbon synthesis catalyst composition comprising a sintered combination metal oxide having the following components in stated weight percentage of the catalyst composition:
(a) 5-80 weight percent Fe oxide;
(b) 4-20 weight percent Zn oxide;
(c) 1-5 weight percent K, Rb, or Cs oxide of mixtures thereof; and
(d) 1-10 weight percent Ce oxide.

Further provided is a process for preparing the catalyst composition of this invention comprising the steps of:
(a) slurrying an aqueous suspension of oxides of: iron, zinc; the carbonates of potassium, rubidium, and/or cesium and cerium;
(b) heating the aqueous slurry to a temperature of at least about 90° C.; and
(c) sintering the resulting solid in an oxygen-containing atmosphere, at a temperature in the range of about 800° C. to 1,200° C. until the x-ray diffraction pattern of the solid is substantially that of at least one iron-containing spinel in the form of $Fe_{3-x}M_xO_4$ where M is a Group 11B metal, preferably Zn and x ranges between about 0.05 and about 2.4, in an oxide matrix comprising $CeO_2$.

Still further provided is a hydrocarbon synthesis process comprising the steps of:
(a) contacting a feedstream of $H_2$ and CO in a molar ratio in the range from 0.5 to 3.0, preferably 0.66 to 1.0:1 with the catalyst of this invention at a temperature in the range of about 200° C. to 350° C., a pressure in the range of about 1 to 50 atmospheres (0.1 to 5 MPaA) and a space velocity in the range of about 10 to 10,000 v/v/hr., thereby resulting in a product hydrocarbon mixture containing ethylene and ethane, in which the ethylene/ethane molar ratio is greater than one; and
(b) recovering said product hydrocarbon.

DESCRIPTION OF THE PREFERRED EMBODIMENTS

The catalysts of the present invention consist of a sintered combination of metal oxides whose composition expressed as weight percentage of the catalyst composition as individual metal oxides is: 5-80 weight percent of a Group VIII metal, preferably Fe oxide as $Fe_2O_3$; 4-20 weight percent of a Group IIB metal oxide, preferably Zn oxide as ZnO; 1-5 weight percent of K, Rb and/or Cs oxide as $K_2O$, $Rb_2O$ and/or $Cs_2O$; and 1-10 weight percent of an oxide of an element or elements of the lanthanide and actinide groups, preferably Ce oxide as $CeO_2$. The catalyst, after sintering, contains a series of Fe-Zn spinels dispersed in an evenly distributed $CeO_2$ matrix.

Fe containing precursors useful in providing the catalyst of the instant invention include $Fe_2O_3$, $Fe_3O_4$, as well as iron hydroxide, nitrate, chloride or carbonate, which can be converted to oxides in the high temperature sintering step. A preferred precursor is $Fe_2O_3$. The quantity of the precursor used is adjusted to achieve the desired final composition, after sintering, wherein Fe as the oxide is present at 5-80%, preferably greater than 50%, of the total weight of the final composition.

The Zn component of the instant catalyst can be derived from the oxide, ZnO, organic hydroxide, nitrate, chloride or carbonate, which can be converted to the oxide in the high temperature sintering step. The preferred Zn precursor is ZnO. The level of precursor employed is adjusted so the final composition will contain 4-20 weight percent Zn as the oxide. Zn present in the final composition may be present in that form or in solid solution with Fe oxide as a spinel.

The alkali metal component, K, Rb, Cs or mixtures thereof, is charged as the alkali carbonate, bicarbonate, hydroxide, nitrate, or other salts, which can be converted to oxides, $K_2O$, $Rb_2O$, $Cs_2O$, or mixtures thereof, in the sintering step. These materials are charged such that the final composition will contain alkali at 1-5 weight percent expressed as the oxide, preferably less than 2 weight percent of the final catalyst composition.

The lanthanide component, such as the Ce component, of the instant invention is charged as the oxide or carbonate. These are charged in amounts such that the final composition contains 1-10 weight percent cerium as the oxide, $CeO_2$, preferably from about 2 to about 5 weight percent of the final catalyst composition.

The catalyst precursor mixture is sintered in air at 800-1,200° C. X-ray diffraction indicates that $Fe_3O_4$ and a series of iron containing spinels are formed, i.e., $Fe_{3-x}M_xO_4$, where M is a Group IIB metal, preferably zinc, where x ranges between about 0.05 and about 2.4, and that these components are present in a $CeO_2$ matrix.

Examples of catalyst compositions considered useful in the conversion of $CO/H_2$ to α-olefins include oxide mixtures of Fe/Zn/Ce/K wherein the metal atom ratios Fe:Zn:Ce:K are 0.8-1.2:0.05-0.08:0.15-0.045:0.15-0.045 and, preferably, 1.0:0.065:0.30:0.030, respectively.

The Ce/K metal atom ratio can be varied from about 3/1 to 1/3 while a preferred ratio is about 1/1.

The sintered metal oxide catalyst of this invention are red-brown or red-purple in color, have BET surface areas $<2m^2/g$, and are highly crystalline in nature as shown by x-ray diffraction. Powder diffraction analysis shows them to consist of a complex mixture of phases, including hematite, magnetite, and a series of mixed spinels $Fe_{3-x}M_xO_4$ wherein M is a Group IIB metal, preferably zinc, x ranges between about 0.05 and about 2.4, all in the presence of a discernible $CeO_2$ phase. The combined chemical and physical properties of these catalysts are thought to influence its behavior under CO hydrogenation reaction conditions.

EXAMPLE 1

Preparation of Fe/Zn/K/Ce Catalyst

The following metal oxides were mixed in a blender: iron oxide as $Fe_2O_3$, ZnO, $CeO_2$ in the following proportions by weight: 1.0:0.065:0.030 taken as gram atoms of free metal. An aqueous slurry of these oxides was then prepared and $K_2CO_3$ added so as to contain 0.03 gram atoms of potassium as the free metal. The water was removed at 100° C. and 10 mm Hg pressure and the final mixture dried at 90° C. for 12 hours. The mixture was sintered by heating at a temperature of about 1,050° C. in air for 24 hours, followed by reduction in a $H_2$ atmosphere at about 500° C. for 7 hours, then passified by exposure to 1 percent $O_2$ in He at 25° C.

Hydrocarbon Synthesis Run

Five to ten grams of the above-prepared catalyst were placed into a stainless steel fixed-bed reactor, 0.95 cm in diameter. The catalyst was pretreated by heating at a temperature of 500° C. in a 9:1 $H_2:N_2$ atmosphere at a pressure of 100 psia and space velocity of 100 v/v cat/hour, for 5-8 hours. X-ray diffraction analysis showed that not all of the metal oxides were completely reduced. After pretreatment, the catalyst was contacted with a 1.8:1 $H_2$:CO molar ratio gaseous feedstream at a space velocity of 1,000 v/v cat/hour and pressure of 300 psig at a temperature of from 250° C. to 270° C. Results of experiments conducted in this manner are provided in Tables I and II.

TABLE I

| Time on Stream | 1 hour | 7 hours |
|---|---|---|
| Temperature-Furnace, °C. | 250 | 250 |
| CO Conversion, % | 98 | 92 |
| $CH_4$, wt. % | 4.4 | 3.2 |
| $CO_2$, wt. % | 47.7 | 43.3 |
| $C_2$-$C_4$ Olefin/Paraffin Ratio | 5.15 | 6.14 |

As is seen from the data, the catalyst of the present invention provides high conversion, low methane selectivity and a $C_2$-$C_4$ fraction rich in α-olefins for periods of time exceeding 1 hour.

TABLE II

| Temperature-Furnace °C. | 270 | 270 |
|---|---|---|
| Bed Temperature Maximum, °C. | 283 | 280 |
| Ratio $H_2$/CO | 1.65 | 3.9 |
| Conversion CO, % | 98 | 98 |
| $CH_4$, Wt. % | 3.0 | 8.8 |
| $CO_2$, Wt. % | 40 | 44 |
| Olefin/Paraffin Ratio | | |
| $C_2$ | 3.1 | 4.3 |
| $C_3$ | 7.8 | 5.85 |
| $C_4$ | >15 | 13.3 |
| $C_5$ | 7.5 | 4.5 |
| $C_6$ | 4.61 | 3.4 |

As is seen from the data, the catalyst of the present invention is able to generate a $C_2$-$C_4$ fraction rich in α-olefins from hydrogen rich feed gas, i.e., with an $H_2$/CO feed ratio in the range of 1.65 to 3.90.

EXAMPLE 2

Catalyst

The catalyst from Example 1 was mixed with an equal volume of solid powdered quartz in a catalyst-:quartz weight ratio of 0.95:1.0.

Pretreatment 18.0 grams of the above-mixed catalyst system was placed into the reactor described in Example 1 and pretreated according to the same procedure.

Hydrocarbon Synthesis Run

Following the above pretreatment, the catalyst was contacted with a 1.82:1.0 $H_2$/CO feedstream under the conditions described in Example 1 for the "non-diluted" catalyst. The results are tabulated below in Tables III and IV.

TABLE III

| Time on Stream | 80 hours | 92 hours |
|---|---|---|
| Temperature-Furnace, °C. | 250 | 250 |
| CO Conversion, % | 53 | 47 |
| $CH_4$, wt. % | 3.3 | 3.2 |
| $CO_2$, wt. % | 29.4 | 27.0 |
| $C_2$-$C_4$ Olefin/Paraffin Ratio | 3.57 | 3.92 |

As is seen from the data of Table III, the catalyst when operated in a diluted bed continues to generate a $C_2$-$C_4$ fraction rich in α-olefins with less than 5 percent weight selectivity to methane, but the apparent activity is lower than that observed in Example 1, presumably due to better temperature control in the catalyst bed.

TABLE IV

| Temperature-Furnace, °C. | 270 |
|---|---|
| Bed Temperature Maximum, °C. | 276 |
| Ratio $H_2$/CO | 2.8 |
| Conversion CO, % | 80 |
| $CH_4$, wt. % | 5.2 |
| Olefin/Paraffin Ratio, $CO_2$, wt. % | 35 |
| $C_2$ | 2.0 |
| $C_3$ | 6.6 |
| $C_4$ | 4.0 |
| $C_5$ | 3.61 |
| $C_6$ | 2.5 |

As is seen from the data of Table IV, the catalyst of the present invention provides greater than 80 percent CO conversions, low methane selectivity and a $C_2$-$C_4$ fraction rich in α-olefins when operated in a nearly isothermal bed, i.e., 270° C.-276° C. temperature range, with a hydrogen rich feed.

EXAMPLE 3

The catalyst prepared in Example 1 and a conventional analog designated as Fe/K, prepared by the procedure described in Example 1 from a mixture of $Fe_2O_3$ and $K_2CO_3$ in the relative proportions 100:1 expressed as the gram ratio of the free metals, were examined under the hydrocarbon synthesis conditions indicated below.

Hydrocarbon Synthesis Run

Approximately 8.8 grams of each of the above-described catalysts were placed into the reactor apparatus and pretreated according to the procedure described in Example 1.

Each catalyst was then contacted with 1.7:1.0 $H_2$/CO feedstream at a space velocity pf 550 v/v/hr., a pressure of 300 psig, at a temperature of 280° C. for 10.5 hours on stream. The product distribution and percent CO conversion at the end of that time were determined at the end of the run by gas chromatographic techniques using nitrogen as an internal standard. The results of the runs are listed below in Table V.

TABLE V

Performance of 1% K/$Fe_2O_3$ and Fe/Ce/Zn/K With Hydrogen Rich Synthesis Gas

| Catalyst | 1% K/$Fe_2O_3$ | Fe/Ce/Zn/K |
|---|---|---|
| CO Conversion, % | 96.0 | 98.0 |
| Wt. % Selectivity | | |
| $CH_4$ | 9.4 | 3.0 |
| $C_2$-$C_6$ | 50.1 | 36.0 |
| $C_7$+ | 14.5 | 21.4 |
| $CO_2$ | 26.0 | 39.6 |
| Olefin:Paraffin Ratio | | |
| $C_2$ | 2.5 | 3.1 |
| $C_3$ | 8.0 | 7.5 |
| $C_4$ | 8.3 | 15.0 |
| $C_5$ | 3.7 | 7.5 |
| $C_6$ | 2.0 | 4.6 |

Conditions:
280° C., 1.7:1.0 $H_2$:CO, 550 v/v/hr, 300 psig, 10.5 hr. on stream. $C_7$+ determined by nitrogen internal standard.

As is seen from the data, the catalyst of the present invention provides greater activity, lower methane selectivity and greater $C_2$-$C_6$ α-olefin selectivity than the conventional catalyst.

EXAMPLE 4

Using the diluted catalyst in Example 2 and the apparatus and pretreatment procedure described in Example 1, the following hydrocarbon synthesis runs were conducted under the conditions described below in Table VI.

TABLE VI

| Fe—Ce—Zn—K 50% Diluted Bed | | |
| --- | --- | --- |
| Standard Hourly Space Velocity (SHSV) | 2000 | 1000 |
| CO Conversion, % | 81 | 95 |
| To Hydrocarbon | 37 | 51 |
| To $CO_2$ | 44 | 44 |
| Hours on Stream | 12 | 24 |
| Wt. % Selectivity | | |
| $CH_4$ | 7.8 | 9.3 |
| $C_2$ | 10.2 | 9.7 |
| $C_2°$ | 2.0 | 3.0 |
| $C_3^=$ | 18.4 | 17.9 |
| $C_3°$ | 1.8 | 1.9 |
| $C_4^=$ | 10.9 | 9.6 |
| $C_4°$ | 1.8 | 1.8 |
| $C_5^=$ | 7.6 | 6.6 |
| $C_5°$ | 1.2 | 1.1 |
| $C_6^+$ | 38.3 | 39.1 |

Conditions:
270° C., 1.8:1 $H_2$:CO, 300 psig.

As is seen from the data, the catalyst of the present invention provides high productivity of $C_2$-$C_6$ α-olefins at high $H_2$/CO feed rates, SHSV=2,000 v/v cat/hour.

EXAMPLE 5

Using the catalyst and apparatus described in Example 1 and the pretreatment procedure described in Example 2, hydrocarbon synthesis runs were conducted, with the results listed below in Table VII:

TABLE VII

| | Fe—Ce—K—Zn | |
| --- | --- | --- |
| | 50% Diluted Bed | Undiluted Bed |
| Hours on Stream | 60 | 60 |
| CO Conversion, % | 86.7 | 82 |
| Wt. % Selectivity | | |
| $CO_2$ | 45.1 | 57.0 |
| $CH_4$ | 4.2 | 10.9 |
| $C_2^=$ | 1.1 | 4.6 |
| $C_2°$ | 0.1 | 6.5 |
| $C_3^=$ | 7.8 | 18.0 |
| $C_3°$ | 0.7 | 3.0 |
| $C_2^=/C_2°$ | 1.1 | 0.7 |
| $C_3^=/C_3°$ | 11.1 | 6.0 |

Conditions:
270-280° C., 1.8:1 $H_2$:CO, 1,000 v/v/hr., 300 psig.

As is seen from the data, the catalyst of the present invention provides higher $C_2$-$C_3$ α-olefin selectivity and lower methane selectivity when operated in a diluted catalyst bed. Thus, it appears that the more isothermal operation possible in the latter configuration allows for optimal selectivity with the catalyst of the present invention.

What is claimed is:

1. A hydrocarbon synthesis catalyst comprising a sintered combination of metal oxides having the following components:
   (a) an oxide of a Group VIII metal;
   (b) an oxide of a Group IIB metal;
   (c) an oxide of a Group IA alkali metal; and,
   (d) an oxide of a lanthanide metal,
   such that said sintered combination comprises a series of the Group VIII metal and the Group IIB metal spinels and the alkali metal oxide dispersed in a lanthanide metal oxide matrix.

2. The composition of claim 1 wherein the range of composition of the components is as follows:
   (a) 5-80 weight percent Group VIII metal oxide;
   (b) 4-20 weight percent Group IIB metal oxide;
   (c) 1-5 weight percent Group IA alkali metal oxide; and,
   (d) 1-10 weight percent lanthanide metal oxide.

3. The composition of claim 2 wherein the Group VIII metal oxide comprises iron oxide.

4. The composition of claim 3 wherein the Group IIB metal comprises zinc oxide.

5. The composition of claim 4 wherein the Group IA alkali metal oxide is selected from the group consisting of potassium oxide, rubidium oxide, cesium oxide and mixtures thereof.

6. The composition of claim 5 wherein the lanthanide oxide comprises cerium oxide.

7. A hydrocarbon synthesis catalyst comprising a sintered combination of metal oxides having the following components in the stated weight percentage of the catalyst composition:
   (a) 5-80 weight percent Fe oxide;
   (b) 4-20 weight percent Zn oxide;
   (c) 1-5 weight percent K, Rb and/or Cs oxide; and,
   (d) 1-10 weight percent Ce oxide,
   such that said sintered combination comprises a series of Fe and Zn spinels and oxides of K, Rb, Cs or mixtures thereof, dispersed in a Ce oxide matrix.

8. The catalyst composition of claim 7 wherein said spinel is magnetite of $Fe_{3-x}Zn_xO_4$, or a series of mixed spinels $Fe_{3-x}Zn_xO_4$, where x ranges between about 0.05 and about 2.4.

9. The catalyst composition of claim 7 wherein said Ce oxide is present in an evenly distributed matrix.

10. The catalyst composition of claim 7 wherein component (c) is K oxide.

11. The catalyst composition of claim 7 wherein component (d) is present as 2 to 5 weight percent of the catalyst composition.

12. A process for preparing the catalyst composition of claim 7 comprising the steps of:
   (a) slurrying an aqueous suspension of oxides and/or carbonates of iron; oxides and/or carbonates of zinc; the carbonates of potassium, rubidium, cesium or mixtures thereof; and cerium carbonate;
   (b) heating the aqueous slurry to at least about 90° C.; and
   (c) sintering the resulting solid in an oxygen-containing atmosphere, at a temperature in the range of about 800° C. to 1,200° C. until the x-ray diffraction pattern of the solid is substantially that of at least one iron-containing spinel, an oxide of potassium, rubidium, cesium or mixture thereof, and $CeO_2$.

* * * * *